United States Patent
Pieper et al.

(10) Patent No.: US 12,151,053 B2
(45) Date of Patent: Nov. 26, 2024

(54) REFILL FOR HOLDING VOLATILE MATERIALS

(71) Applicant: S. C. JOHNSON & SON, INC., Racine, WI (US)

(72) Inventors: Gregory G. Pieper, Spring Grove, IL (US); Ryan Stolzenbach, Racine, WI (US); Jesse Richard, Racine, WI (US); Richard D. Maggard, Jr., Oak Creek, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 16/045,165

(22) Filed: Jul. 25, 2018

(65) Prior Publication Data

US 2019/0091365 A1    Mar. 28, 2019

Related U.S. Application Data

(63) Continuation-in-part of application No. 15/713,206, filed on Sep. 22, 2017, now Pat. No. 10,258,710.

(51) Int. Cl.
*A61L 9/12* (2006.01)
*A61M 21/00* (2006.01)
(Continued)

(52) U.S. Cl.
CPC .............. *A61L 9/127* (2013.01); *A61M 21/00* (2013.01); *B65D 1/0246* (2013.01);
(Continued)

(58) Field of Classification Search
CPC ............... A61L 9/127; A61L 2209/133; A61L 9/00–22; A61L 9/037; A61L 9/12;
(Continued)

(56) References Cited

U.S. PATENT DOCUMENTS 3,802,590 A    4/1974 Culver
3,822,811 A    7/1974 Landen
(Continued)

FOREIGN PATENT DOCUMENTS

EP    1640039 B1    4/2009
EP    1331014 B1    2/2012
(Continued)

OTHER PUBLICATIONS

International Search Report and Written Opinion issued in corresponding International Application No. PCT/US2018/052052, dated Apr. 12, 2019, 21 pages.

(Continued)

*Primary Examiner* — Joseph A Greenlund
*Assistant Examiner* — Juan C Barrera
(74) *Attorney, Agent, or Firm* — Quarles & Brady LLP

(57) ABSTRACT

A refill for dispensing a volatile material includes a bottle having a body defined by at least one sidewall and a neck extending from the body. The neck includes a rim at an upper end thereof and has an inner surface, a top surface, and an outer surface. A wick has a first end positioned within the bottle and a second end extending out of the bottle. A plug assembly is secured to the neck of the bottle and retains the wick within the bottle. A cap is coupled with the neck of the bottle. An underside of the cap includes a stop and a flange that form a seal with the plug assembly when the refill is in an assembled configuration.

20 Claims, 11 Drawing Sheets

(51) Int. Cl.
    *B65D 1/02*       (2006.01)
    *B65D 41/04*      (2006.01)

(52) U.S. Cl.
    CPC .... *B65D 41/0421* (2013.01); *A61L 2209/133* (2013.01); *A61M 2021/0016* (2013.01); *A61M 2209/045* (2013.01)

(58) Field of Classification Search
    CPC .............. B65D 1/0246; B65D 41/0421; B65D 1/00–48; B65D 41/00–62; B65D 1/023; B65D 1/0223; B65D 11/02; B65D 41/0428; B65D 41/325; B65D 41/34; B65D 41/04; B65D 41/0407; B65D 47/122; B65D 47/123; B05B 17/0684; B05B 17/0676; A61M 21/00; A61M 2021/0016; A61M 2209/045; Y10S 215/01; Y10S 261/88
    USPC ............................ 215/44, 43, 40; 239/34–60
    See application file for complete search history.

(56) References Cited

U.S. PATENT DOCUMENTS

| | | | |
|---|---|---|---|
| 4,919,981 | A | 4/1990 | Levey |
| 5,489,036 | A * | 2/1996 | Arkins ............... B65D 41/0421 |
| | | | 215/343 |
| 5,725,152 | A | 3/1998 | Akyu |
| 6,104,867 | A | 8/2000 | Stathakis et al. |
| 6,446,880 | B1 * | 9/2002 | Schram ............... B05B 17/0646 |
| | | | 222/570 |
| 6,768,865 | B2 | 7/2004 | Stathakis et al. |
| 6,779,672 | B2 | 8/2004 | Kano et al. |
| 6,792,199 | B2 | 9/2004 | Levine et al. |
| 7,014,055 | B2 | 3/2006 | Kano et al. |
| 7,017,829 | B2 | 3/2006 | Martens, III et al. |
| 7,244,398 | B2 | 7/2007 | Kotary et al. |
| 7,303,143 | B2 | 12/2007 | Davis et al. |
| 7,352,960 | B2 | 4/2008 | Hafer et al. |
| 7,389,943 | B2 | 6/2008 | Jaworski |
| 7,416,766 | B2 | 8/2008 | Trent et al. |
| 7,643,734 | B2 | 1/2010 | Wefler |
| 7,743,952 | B2 | 6/2010 | Auer et al. |
| 7,832,579 | B2 | 11/2010 | Lohrman et al. |
| 7,886,899 | B2 | 2/2011 | Frutin |
| 8,025,189 | B2 | 9/2011 | Salameh |
| 8,235,232 | B2 | 8/2012 | Isogai et al. |
| 8,485,398 | B2 | 7/2013 | Kneer |
| 8,496,129 | B2 | 7/2013 | Isogai et al. |
| 9,375,739 | B2 | 6/2016 | Ivri |
| 9,694,967 | B2 | 7/2017 | Salameh |
| 9,849,206 | B1 | 12/2017 | Hsiao |
| 2004/0026464 | A1 | 2/2004 | Granger et al. |
| 2005/0195598 | A1 | 9/2005 | Dancs et al. |
| 2005/0211579 | A1 | 9/2005 | Makita |
| 2005/0284952 | A1 | 12/2005 | Davis et al. |
| 2006/0175425 | A1 | 8/2006 | McGee et al. |
| 2006/0289570 | A1 | 12/2006 | Rohr et al. |
| 2007/0080128 | A1 | 4/2007 | Laveault et al. |
| 2009/0261179 | A1 | 10/2009 | Hall |
| 2010/0059601 | A1 | 3/2010 | Bankers et al. |
| 2010/0215549 | A1 | 8/2010 | Corda |
| 2011/0139892 | A1 | 6/2011 | Gasper |
| 2012/0000880 | A1 * | 1/2012 | Im ...................... B65D 51/2864 |
| | | | 215/316 |
| 2012/0312893 | A1 * | 12/2012 | Santini ..................... A61L 9/12 |
| | | | 239/44 |
| 2013/0037580 | A1 | 2/2013 | Armstrong et al. |
| 2013/0327327 | A1 | 12/2013 | Edwards et al. |
| 2015/0321798 | A1 * | 11/2015 | Isogai .................... B65D 39/08 |
| | | | 215/253 |
| 2015/0367366 | A1 | 12/2015 | Edwards et al. |
| 2016/0263602 | A1 | 9/2016 | Ivri |
| 2016/0311589 | A1 | 10/2016 | Wochele |
| 2017/0036824 | A1 | 2/2017 | King |
| 2019/0091365 | A1 | 3/2019 | Pieper |

FOREIGN PATENT DOCUMENTS

| | | |
|---|---|---|
| EP | 3326489 A1 | 5/2018 |
| FR | 2804662 B1 | 5/2002 |
| FR | 2839296 A1 | 11/2003 |
| JP | H0335055 U | 4/1991 |
| JP | 2000238822 A | 9/2000 |
| JP | 2009082649 A | 4/2009 |
| JP | 4276726 B2 | 6/2009 |
| WO | 9113637 W | 9/1991 |
| WO | 9800177 W | 1/1998 |
| WO | 2019060615 A2 | 3/2019 |

OTHER PUBLICATIONS

International Search Report and Written Opinion issued in corresponding International Application No. PCT/US2019/037684, will be mailed Mar. 5, 2020, 19 pages.

Mexican Patent Office, Second Office Action for Application MX/a/2020/003108 dated May 23, 2024, 5 pages.

* cited by examiner

REFILL FOR HOLDING VOLATILE MATERIALS

CROSS REFERENCE TO RELATED APPLICATIONS

This application is a continuation-in-part of U.S. application Ser. No. 15/713,206 filed on Jan. 4, 2018, and entitled "CONTAINER FOR HOLDING VOLATILE MATERIALS," the entire disclosure of which is incorporated by reference in its entirety.

BACKGROUND OF THE DISCLOSURE

Various volatile material dispensing devices are known in the prior art and generally comprise a dispenser and one or more refills having one or more volatile materials disposed therein. Typical volatile material dispensing mechanisms used in volatile material dispensing devices include a heating device and/or a fan to assist with the emanation of the volatile material from the refill(s).

Refills for dispensers generally include a bottle, a plug or wick holder that is inserted into a mouth within a neck of the bottle, and a wick that is retained by the plug, the wick having a first end in contact with the volatile material and a second end extending out of the bottle. The volatile material is moved from the bottle, through the first end of the wick to an end of the wick by capillary action. Surfaces defining the mouths of refills have varying geometry, depending on the type of material being used for the bottle itself. Further, the type of material used for such bottles can vary.

Some bottles are made from glass, while some are made from plastic resins such as metallocene polypropylene (mPP) or Barex resins. In the fragrance oil delivery space, clear polymers have been found to develop stress cracking along a neck of the refill surrounding the mouth, especially when exposed to increasing temperature and/or bottle stress. While a portion of the stress cracking is believed to be due to selective absorption of stress cracking agents, i.e., from fragrance oils and/or solvents, a portion of the stress cracking is likely due to hoop or circumferential stress incurred by the bottle after the plug and wick have been inserted therein and after a cap is attached to the refill. It is believed that these stress cracking agents cause the formation of micro-yielded or stress-dilated zones, which reduce the yield strength of the polymer forming the bottle. A reduction in yield strength of the polymer can lead to crack initiation and fracture, which may worsen upon insertion of the plug and/or wick and/or after attachment of the cap.

Much of the stress cracking of typical refill bottles comprising polymers forms in the neck of the bottle, e.g., adjacent the mouth. Stress cracking is typically a result of stress on portions of the refill bottle. Because of the clamping of the neck by the wick holder, a number of stresses are created along an uppermost portion of the neck. In many instances, the stress cracking originates from a sealing surface and propagates to a medial portion of the neck. Since refill bottles must retain the fluid held therein, it is desirable to maintain a fluid seal between the plug and the bottle, and to also reduce the stress cracking that propagates adjacent the neck of the bottle. It would therefore be desirable to minimize the plug assembled tensile hoop stress that develops in the bottle neck finish while maintaining a normal seal pressure.

SUMMARY

According to one aspect, a refill for dispensing a volatile material includes a bottle having a body defined by at least one sidewall and a neck extending from the body, the neck comprising a rim at an upper end thereof, the rim being defined by an inner surface, a top surface, and an outer surface. The refill further includes a wick having a first end positioned within the bottle and a second end extending out of the bottle, a plug assembly secured to the neck of the bottle that retains the wick within the bottle, and a cap coupled with the neck of the bottle. An underside of the cap comprises a stop and a flange that form a seal with the plug assembly when the refill is in an assembled configuration.

According to another aspect, a refill for dispensing a volatile material includes a bottle having a body defined by at least one sidewall and a neck extending from the at least one sidewall, the neck comprising threading circumscribing at least a portion of the neck, and a rim at an upper end of the neck, the rim defined by an inner surface, an outer surface, and a top surface extending between the inner and outer surfaces. A channel is formed by the neck and a longitudinal axis is defined by the channel. The refill further includes a wick having a first end positioned within the bottle and a second end extending out of the bottle, the wick being positioned within the channel. The refill also includes a plug assembly coupled to the neck of the bottle, the plug assembly retaining the wick within the bottle, and a cap attached to the bottle, the cap comprising a stop and a flange that depend from an underside of the cap. The flange applies a force against a first wall of the plug assembly when the cap is attached to the bottle.

DETAILED DESCRIPTION OF THE DRAWINGS

The present disclosure is directed to refills for volatile material dispensers capable of vaporizing and dispensing volatile materials. While the devices disclosed herein may be embodied in many different forms, several specific embodiments are discussed herein with the understanding that the embodiments described in the present disclosure are to be considered only exemplifications of the principles described herein, and the disclosure is not intended to be limited to the embodiments illustrated. Throughout the disclosure, the terms "about" and "approximately" mean plus or minus 5% of the number that each term precedes.

The use of the term "volatile material" herein refers to any volatile material that a consumer may desire to emit into an area surrounding one or more refills holding the volatile material(s) and/or a dispenser holding one or more refills. Illustratively, the types of volatile materials may be, for example, a cleaner, an insecticide, an insect repellant, an insect attractant, a mold or mildew inhibitor, a fragrance, a disinfectant, an air purifier, an aromatherapy scent, an antiseptic, a positive fragrancing volatile material, an air-freshener, a deodorizer, or the like, and/or combinations thereof. Additives may be included in the volatile material, such as, for example, fragrances and/or preservatives.

Figure 1:
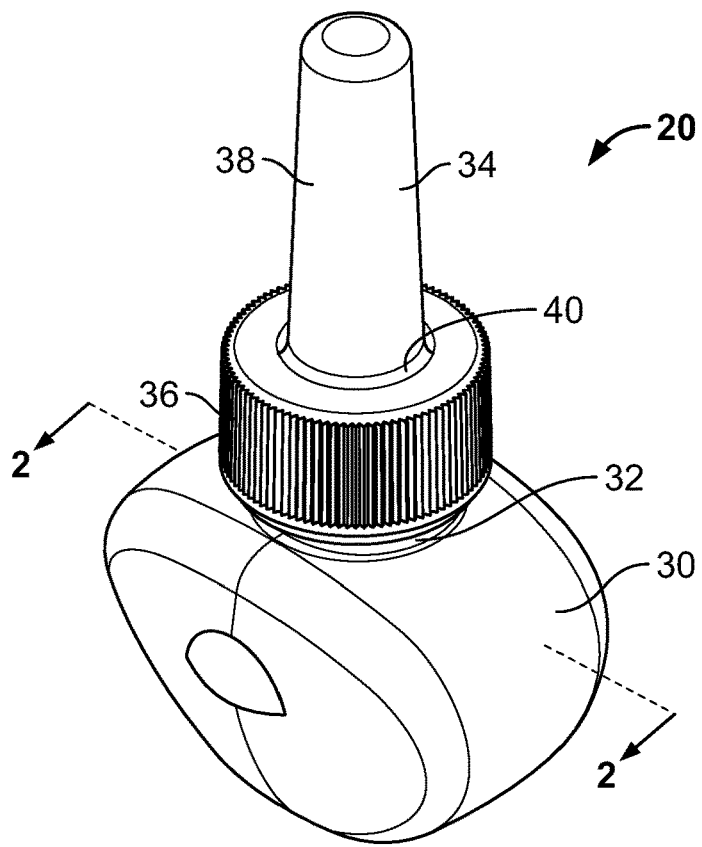
FIG. 1 is a front, top isometric view of a refill according to some aspects of the present disclosure.
Figure 2:
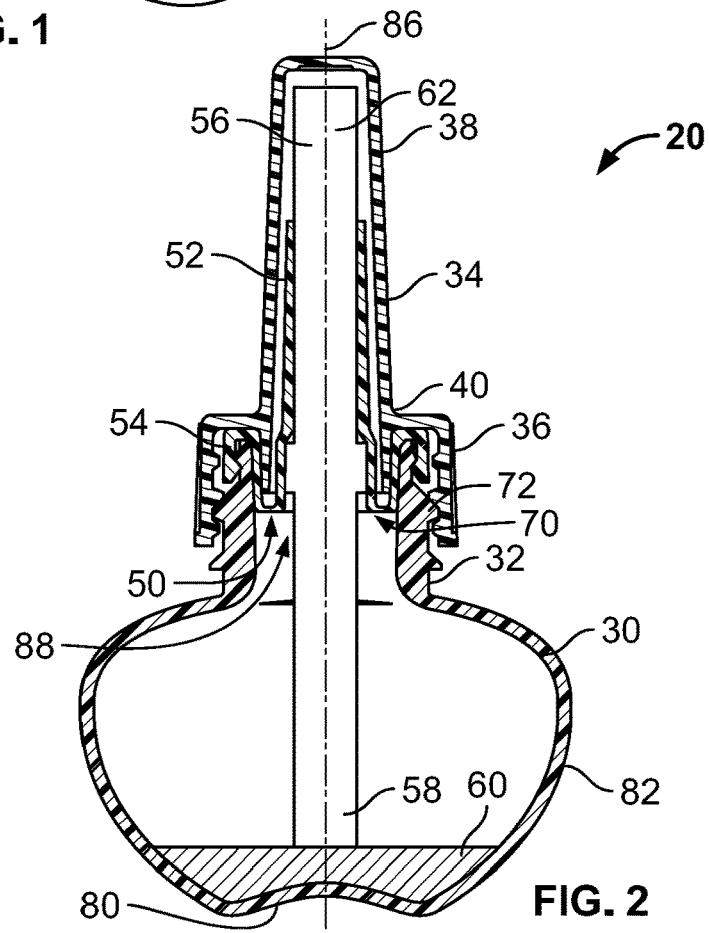
FIG. 2 is a cross-sectional view taken generally along the lines 2-2 of FIG. 1.
Figure 3:
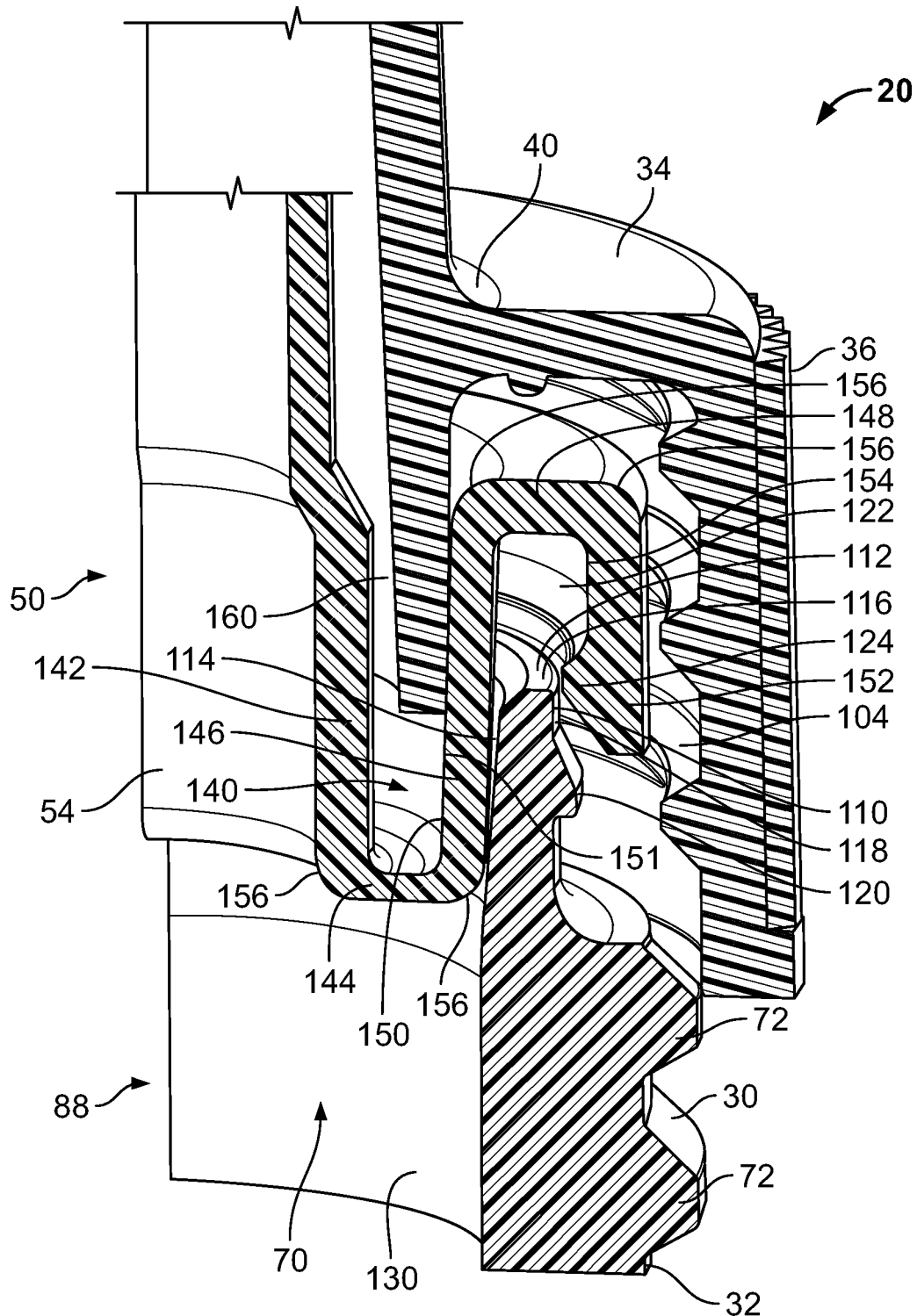
FIG. 3 is a partial cross-sectional view of the refill of FIG. 2, without a wick, and in a partially exploded configuration.

FIGS. 1-3 generally depict a refill 20 for use with a volatile material dispenser (not shown) that may be capable of actively or passively emanating a volatile material disposed within the refill 20 into the ambient environment. In some embodiments, the refill 20 is capable of insertion into and retention within the volatile material dispenser. Referring now to FIG. 1, the refill 20 generally includes a bottle 30 that holds a volatile material, wherein a cylindrical neck 32 extends upwardly from the bottle 30. The bottle 30 may be formed from glass, a polymer, or another suitable material or materials. A cap 34 is shown secured to the neck 32 of the bottle 30. The cap 34 generally includes a securement portion 36 and a cover portion 38. The securement portion 36 may include threading along an inner surface thereof that may be used to secure the cap 34, for example, to the neck 32 of the bottle 30. The securement portion 36 and the cover portion 38 are connected at a joint 40.

Referring to FIG. 2, a front cross sectional view of the refill 20 is shown. As illustrated in FIG. 2, the refill 20 further includes a plug assembly 50 that is disposed within and attached to the neck 32 of the refill 20. The plug assembly 50 generally includes a sheath 52 and a base 54. The plug assembly 50 retains a wick 56 centrally within the bottle 30 and prevents leakage of volatile material 60 out of the bottle 30. A lower portion 58 of the wick 56 is in fluid communication with the volatile material 60 disposed within the bottle 30. The wick 56 extends upwardly through the neck 32 such that an upper portion 62 thereof is exposed to a surrounding environment when the cap 34 is removed.

The sheath 52 of the plug assembly 50 extends upwardly from a mouth 70 of the bottle 30 and surrounds a portion of the wick 56. The wick 56 may be any type of transportation mechanism such as, for example, typical wicks (of porous material), dip tubes, hollow tubes, and gravity fed surfaces or components, or any other suitable transportation mechanism.

Still referring to FIG. 2, the bottle 30 further includes a bottom wall 80 and at least one sidewall 82. The bottom wall 80 is depicted as being generally concave, however, the bottom wall 80 may be planar, or have any other suitable configuration. As illustrated in FIG. 2, the sidewall 82 extends upwardly from the bottom wall 80 and bows outwardly from a longitudinal axis 86 that extends through the wick 56, when the refill 20 is assembled. The sidewall 82 terminates at the neck 32 of the bottle 30. During assembly of the refill 20, the wick 56 and the sheath 52 are inserted into a channel 88 defined by the neck 32 of the refill 20.

Figure 5:
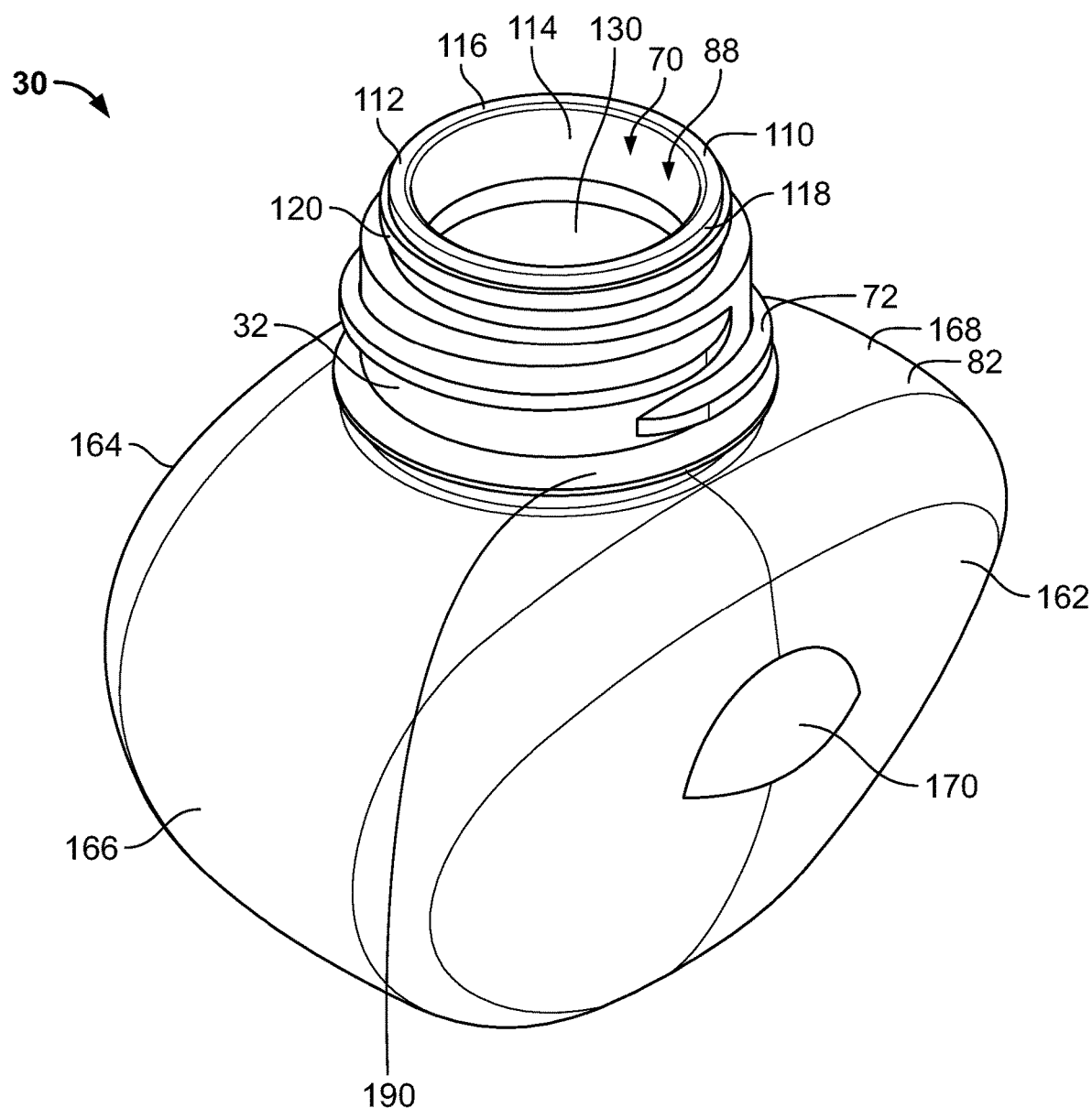
FIG. 5 is a front, top, and side isometric view of a bottle of the refill of FIG. 1.
Figure 6:
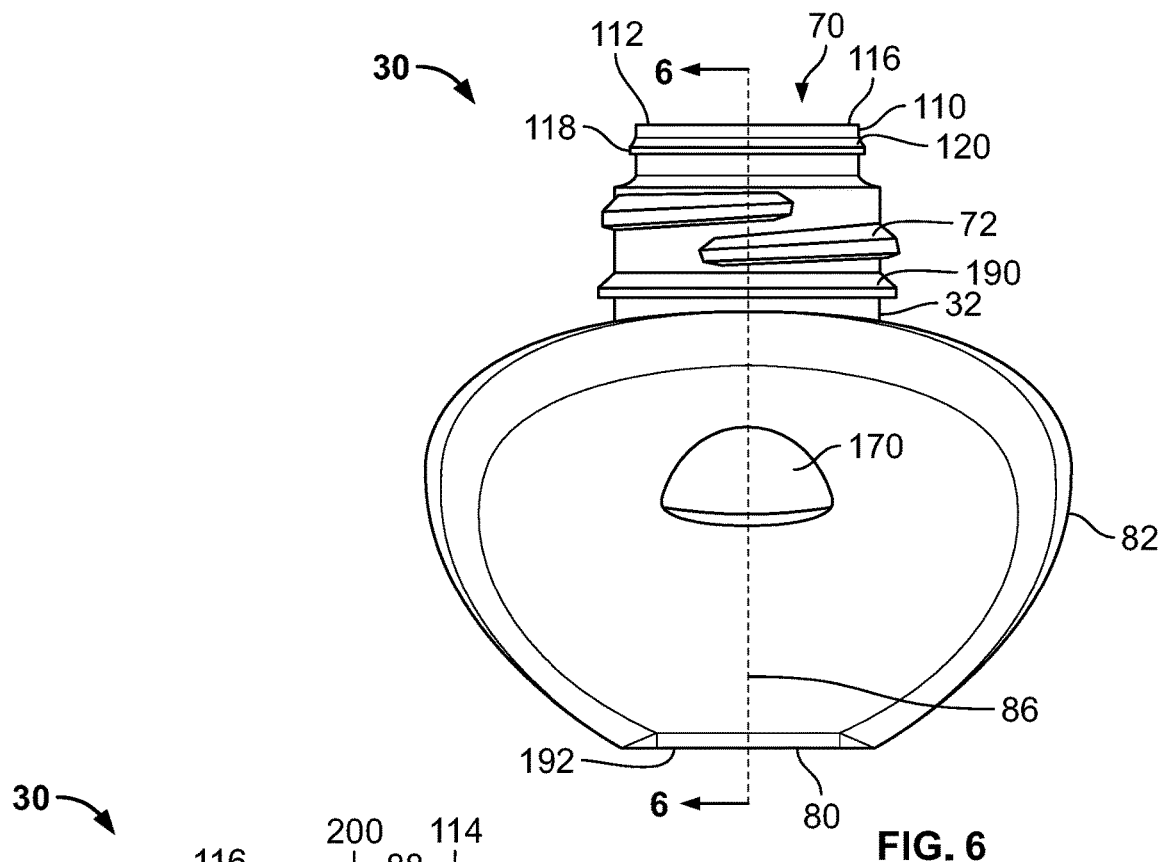
FIG. 6 is a front elevational view of the bottle of FIG. 5.

Referring to FIG. 5, the sidewall 82 of the bottle 30 includes front and rear surfaces 162, 164 and first and second side surfaces 166, 168 connecting the front and rear surfaces 162, 164. The front surface 162 has a generally bulbous central portion and is generally curved inwardly at sides and a bottom thereof. The rear surface 164 may be a mirror image of the front surface 162, or may have a different configuration. In some embodiments, the rear surface 164 is generally planar. In some embodiments, a protrusion or design element 170 extends outwardly from the front surface 162, wherein the design element 170 may function to retain the refill 20 within a dispenser. While the bottle disclosed herein is shown as having a particular shape, the principles of the present disclosure may be applied to a refill having a bottle with any suitable shape.

Figure 4:
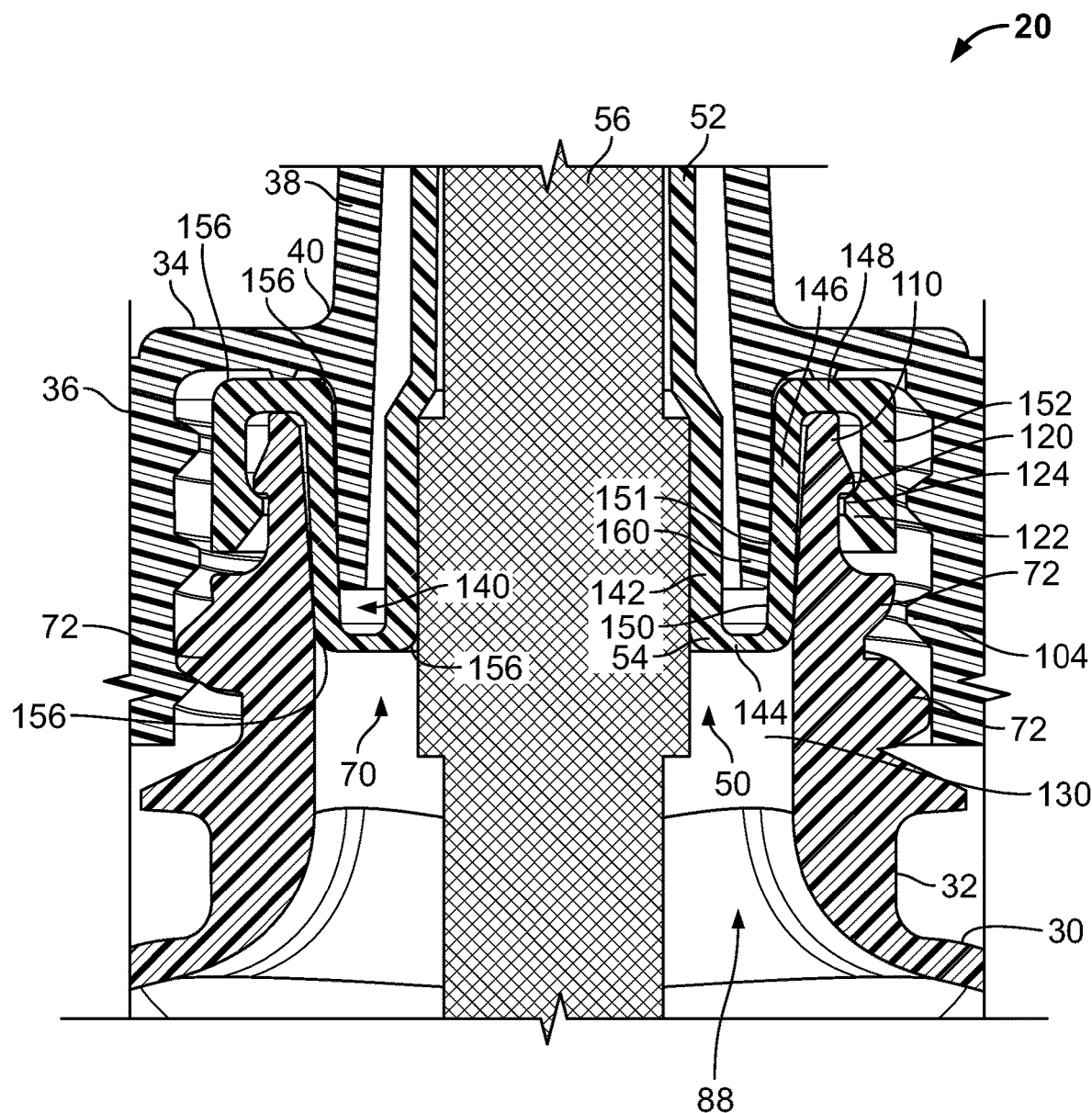
FIG. 4 is another partial cross-sectional view of the refill of FIG. 2.

Referring now to FIGS. 3 and 4, a first thread 72 is disposed on the neck 32 of the bottle 30 to aid in retaining the cap 34 thereon and/or to aid in retaining the refill 20 to or within the dispenser. The cap 34 includes a second thread 104 on an inner surface thereof that corresponds with, and is operable to receive the first thread 72. The first thread 72 and the second thread 104 comprise a securement mechanism that may retain the cap 34 on the bottle 30. In other embodiments, other securement mechanisms may be utilized to retain the cap 34 on the bottle 30. The first and/or second threads 72, 104 may include a single, contiguous thread, a double thread, or some other type of multi-start thread. The first and/or second threads 72, 104 may alternatively be discontinuous.

Referring again to FIG. 3, an annular rim 110 is disposed at an upper end 112 of the neck 32 above the first thread 72. The rim 110 is defined by an interior surface 114, a top surface 116, and an outer surface 118, which will be discussed in greater detail hereinafter below. A first annular protrusion 120 extends outwardly from the neck 32 between the outer surface 118 of the rim 110 and the first thread 72. In some embodiments, the first annular protrusion 120 is included to retain the plug assembly 50, which may include a locking feature 122, as shown in FIGS. 3 and 4. The locking feature 122 may include a second annular protrusion 124 that snaps over the first annular protrusion 120. The neck 32 of the bottle 30 also includes an inner surface 130 that forms the channel 88. While the first and second annular protrusions 120, 124 are described as being annular, the first and second annular protrusions 120, 124 may alternatively be discrete, discontinuous protrusions.

Still referring to FIG. 3, the base 54 of the plug assembly 50 is shown in greater detail. The base 54 includes a well 140 defined by an inner wall 142, a lower wall 144, and an intermediate wall 146. The inner wall 142 and the intermediate wall 146 are substantially parallel. The lower wall 144 joins the inner wall 142 with the intermediate wall 146 and is further substantially perpendicular to each of the inner wall 142 and the intermediate wall 146. An upper wall 148 is joined with, and extends outwardly from the intermediate wall 146. The upper wall 148 is also coupled to an outer wall 152, which is substantially perpendicular to the upper wall 148. The second annular protrusion 124 is disposed along an inner surface 154 of the outer wall 152. In some embodiments, the inner wall 142, the intermediate wall 146, and the outer wall 152 are substantially parallel with respect to one another. In some embodiments, joints 156 between the inner wall 142 and the bottom wall 80, the lower wall 144 and the intermediate wall 146, the intermediate wall 146 and the upper wall 148, and the upper wall 148 and the outer wall 152 are rounded. Any wall or portion defined herein that is referred to as being substantially parallel with respect to another wall or portion may be up to 10 degrees offset from an axis defined by the first wall or portion.

Referring again to FIGS. 3 and 4, the cap 34 includes a seal skirt 160 that extends into the well 140 of the plug assembly 50. The seal skirt 160 may be dimensioned to abut the lower wall 144 of the plug assembly 50, thereby forming a seal therebetween. The seal skirt 160 may also be sized and positioned to provide a pressure or stress against a lower portion 150 of the intermediate wall 146, which can thereby relieve stress along the rim 110 of the neck 32 of the bottle 30. The seal skirt 160 may additionally or alternatively be sized and positioned to provide a pressure or stress against a medial portion 151 of the intermediate wall 146, i.e., a portion above the lower portion 150. The seal skirt 160 may have one or more features attached thereto or extending therefrom that can aid in relieving or displacing stress from the upper portion of the neck 32 of the bottle 30.

As shown in FIG. 4, the plug assembly 50 is secured to the bottle 30, and the cap 34 is secured to the plug assembly 50. The seal skirt 160 is disposed within the well 140 and abuts the medial portion 151 of the intermediate wall 146. Due to the geometry of the cap 34, the seal skirt 160 applies a pressure against the intermediate wall 146. A first seal is formed between the seal skirt 160 and the medial portion 151 of the intermediate wall 146, which is referred to as the "sheath-to-cap" seal. A second seal is formed between the intermediate wall 146 and the inner wall 130 of the neck 32, which is referred to as the "sheath-to-neck" seal. The sheath-to-cap seal and the sheath-to-neck seal prevent volatile from escaping from the refill 20 when the cap 34 is secured to the bottle 30, and when the plug assembly 50 is secured to the bottle, respectively. As such, each of the sheath-to-cap seal and the sheath-to-neck seal may be an air tight seal.

Figure 7:
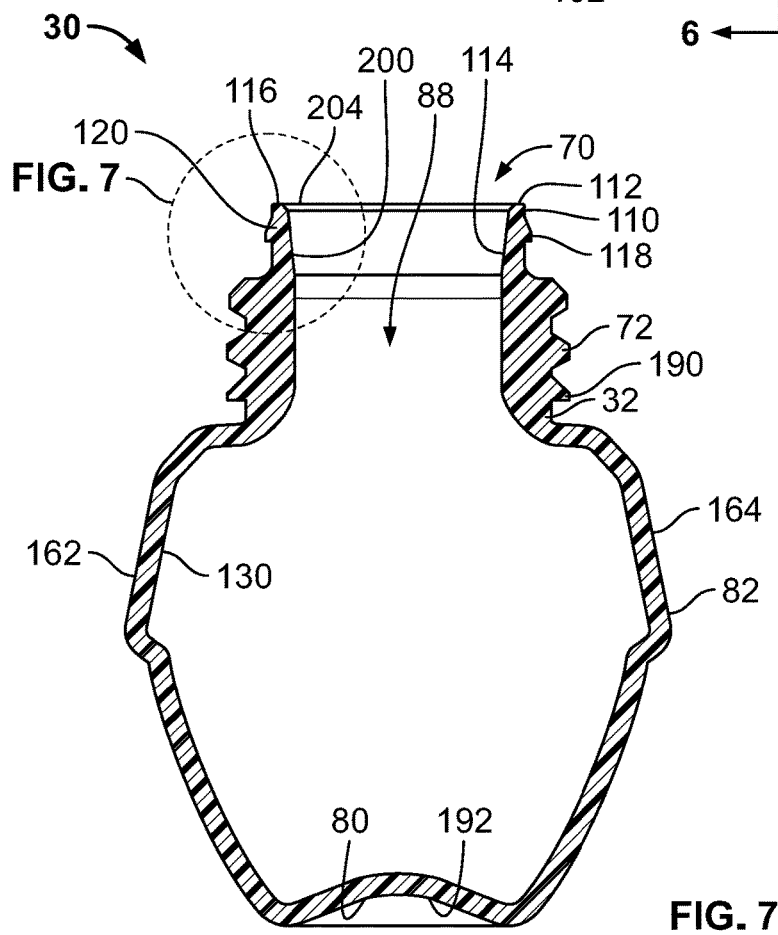
FIG. 7 is a cross-sectional view taken generally along the lines 6-6 of FIG. 6.
Figure 8:
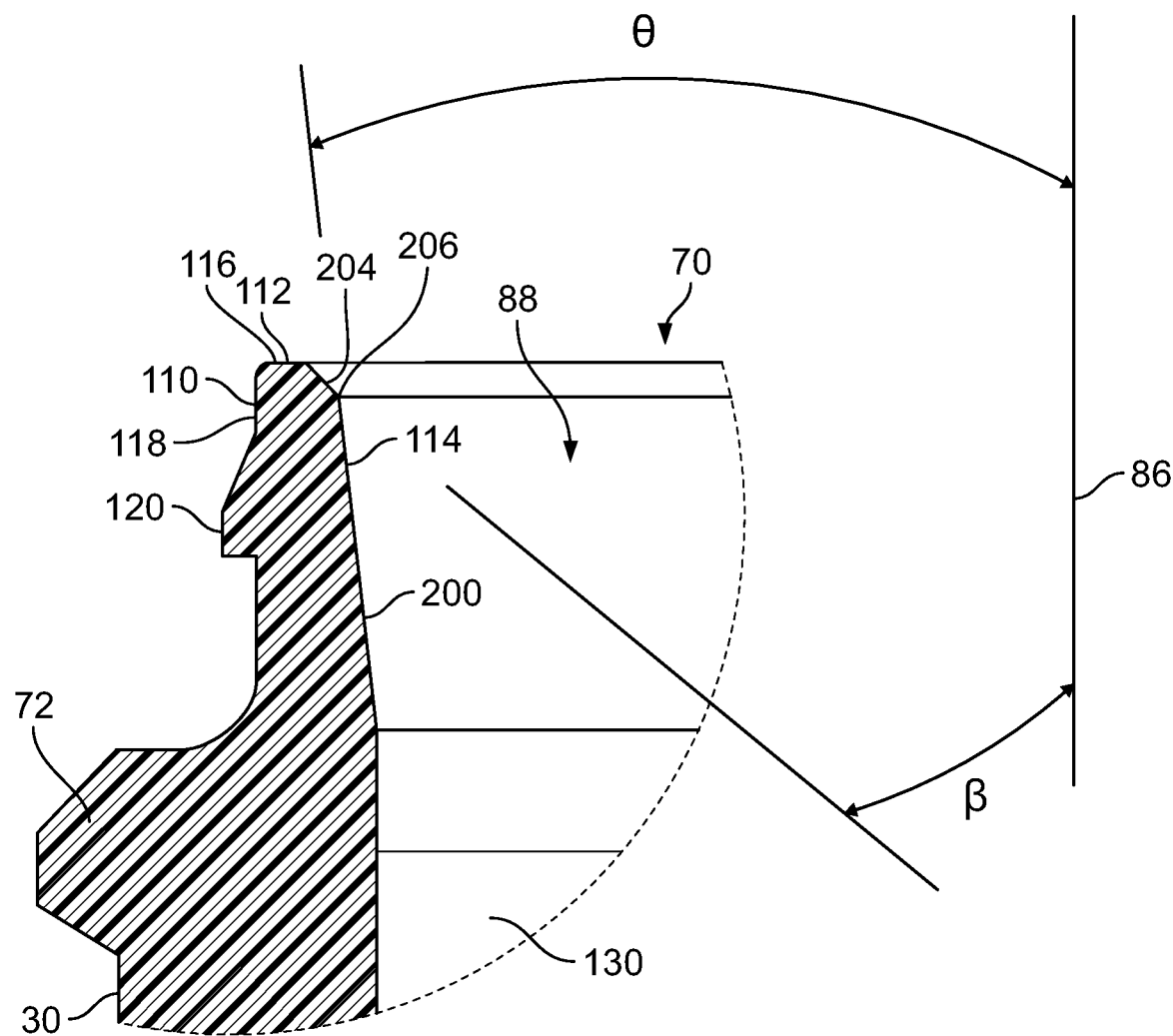
FIG. 8 is a partial cross-sectional view of a neck or finish of the bottle of FIG. 7.

Referring to FIGS. 7 and 8, the configuration of the rim 110 of the bottle 30 will now be discussed in greater detail. Referring specifically to FIG. 8, to reduce the strain on the neck 32 of the bottle 30 and, thus, the stress cracks that can result therefrom, the interior surface 114 of the rim 110 is shown being angled, i.e., the interior surface 114 is a chamfered surface 200. In the embodiment illustrated in FIGS. 7 and 8, the chamfered surface 200 has a chamfer angle $\theta$ of approximately 6 degrees measured from the longitudinal axis 86. However, the chamfered surface 200 may have a chamfer angle $\theta$ of between about 1 degree and about 10 degrees, or between about 2 degrees and about 9 degrees, or between about 3 degrees and about 8 degrees, or between about 4 degrees and about 7 degrees, or about 6 degrees.

In some embodiments, only a single portion or multiple discrete portions of the inner surface 130 of the rim 110 form the chamfered surface 200. In some embodiments, the entire inner surface 130 forms the chamfered surface 200. In some embodiments, the chamfered surface 200 begins at or above an uppermost extent of the first thread 72, as shown in FIG. 8, but the chamfered surface 200 may alternatively begin below an uppermost extent of the first thread 72.

Still referring to FIG. 8, the inner surface 130 of the rim 110 is partially defined by the chamfered surface 200 as well as an angled surface 204 that joins the chamfered surface 200 at an apex 206. The angled surface 204 may have an angle $\beta$ of approximately 45 degrees from the longitudinal axis 86. In some embodiments, the angle $\beta$ of the angled surface 204 is between about 20 degrees and about 70 degrees, or between about 30 degrees and about 60 degrees, or between about 40 degrees and about 50 degrees. The angled surface 204 terminates at the top surface 116 of the rim 110. The top surface 116 is generally perpendicular with respect to the longitudinal axis 86.

The benefits of the chamfered surface 200 will now be discussed. Through testing of existing refills, a high amount of stress was measured in the neck of the bottle. Further, it was determined that during assembly of existing refills, the high points of the stresses are generated at high interference locations, which were determined to be at each of the sheath-to-cap seal and the sheath-to-neck seal, as described above. The inclusion of the chamfered surface 200 was found to reduce stress cracking caused by stresses incurred during and after assembly of the refill 20.

Through experimental testing, it was determined that a chamfered surface 200 of between about 4 degrees and about 7 degrees greatly reduces hoop stress in the neck 32 of the bottle 30 after the sheath 52 is inserted into and retained within the neck 32, thereby reducing or preventing stress-cracking within the bottle neck 32 during assembly and/or when the bottle 30 is exposed to fragrance oils. The compression seal reduction from a first design of the bottle having a two degree chamfer for the sheath-to-neck seal resulted in an 8% stress reduction, and the sheath-to-cap seal resulted in a 6.7% stress reduction. For a five degree chamfered design, the sheath-to-neck seal resulted in a 9% stress reduction, and the sheath-to-cap seal resulted in a 20% stress reduction. It was determined that inclusion of the chamfered surface 200 moves the high interference locations down into the bottle neck by moving the high interference locations away from the bottle neck tip, where cracking typically occurs/originates.

During another test, the seal pressures and tensile hoop stresses developed during assembly of a refill with a six degree chamfer ("chamfered refill") were compared to the tensile hoop stresses developed for an existing mPP-based refill ("existing refill") with no chamfer. During the test, the chamfered refill and the existing refill were each filled with the same fragrance at room temperature, and were each assembled using a torque wrench. Both the chamfered refill and the existing refill were inverted quickly to allow for wetting of the bottle-sheath and sheath-cap contact surfaces. The mPP-based refill was otherwise identical in all relevant aspects (i.e., in the neck of the bottle) to the refill with the six degree chamfer. The seals of the chamfered refill were found to be at or better than the seals of the existing refill.

For the existing refill, the peak sheath-to-neck seal pressure was found to be 1419 psi and the sheath-to-cap seal pressure was between 427 and 540 psi. For the chamfered refill, the sheath-to-neck seal pressure was found to be 1434 psi, while the sheath-to-cap seal pressure was found to be between 520 and 726 psi. Both the chamfered refill and the existing refill were found to generate similar sheath-to-bottle compression seal pressures, while the chamfered refill maintained typical tensile hoop stresses in the neck. Maintaining the compression seals is important to ensure that the fragrance remains within the bottle during transport and use thereof.

While the above embodiments have been described as comprising configurations of refills having one or more stress-reducing features such as a chamfered surface along an interior surface of a finish of a bottle, and/or a seal skirt along an underside of a cap, alternative stress reduction features will now be described. Any of the features as described above may be utilized with or in addition to the stress reducing features described with respect to the embodiments described hereinafter below.

Figure 9:
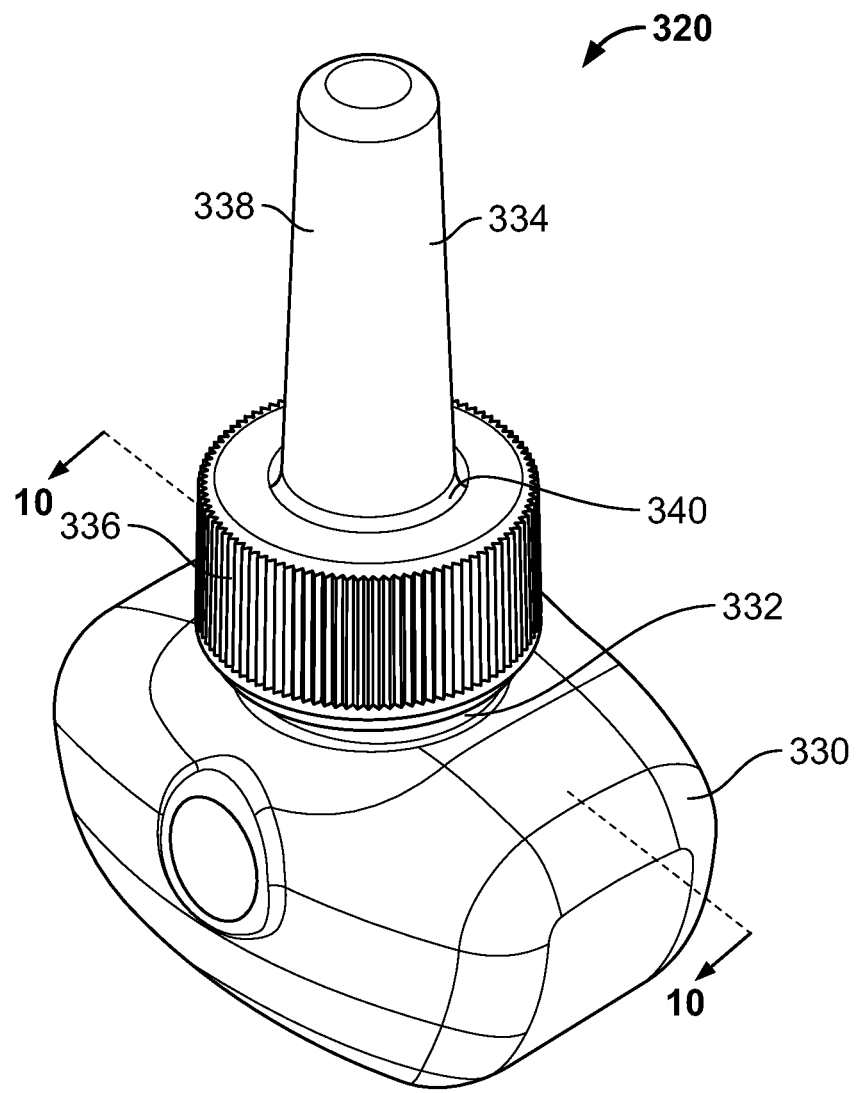
FIG. 9 is a front, top isometric view of another refill according to some aspects of the present disclosure.

Referring now to FIGS. 9-13, a refill 320 is depicted for use with a volatile material dispenser (not shown) that is capable of actively or passively emanating a volatile material disposed within the refill 320 into the ambient environment. As discussed above with respect to the refill 20, the refill 320 is capable of insertion into and retention within the volatile material dispenser. Referring to FIG. 9, the refill 320 generally includes a bottle 330 that holds a volatile material, wherein a cylindrical neck 332 extends upwardly from the bottle 330. The bottle 330 may be similar to or the same as the bottle 30 as described above, or the bottle 330 may a have a different form.

The bottle 330 may be formed from glass, a polymer, or another suitable material or materials. A cap 334 is shown secured to the neck 332 of the bottle 330. The cap 334 generally includes a securement portion 336 and a cover portion 338. The securement portion 336 may include threading along an inner surface thereof that may be used to secure the cap 334, for example, to the neck 332 of the bottle 330. The securement portion 336 and the cover portion 338 are connected at a joint 340. The bottle 330 may have the same or similar sidewall and/or bottom wall configurations as the bottle 30 described above. Alternatively, the bottle 330 may have other forms, and may have features that are different than as described above with respect to the bottle 30.

In some embodiments, the bottle 330 comprises polyethylene terephthalate (PET) and the cap 334 may comprise polypropylene (PP). The PET comprising the bottle 330 may have an elastic modulus of between about 2200 MPa and about 3200 MPA, or between about 2500 MPA and about 2900 Mpa, or about 2750 MPa. The PET may further have a tensile strength of between about 60 MPa and about 100 MPa, or between about 70 MPa and about 90 MPa, or about 80 MPa. The PET may further have a Poisson's ratio of between about 0.2 and about 0.6 or between about 0.3 and about 0.5, or about 0.4. The PET may further comprise a tangent modulus of between about 220 MPa and about 330 MPa, or between about 240 MPa and about 310 MPa, or about 275 MPa. The PET comprising the bottle 330 may further comprise a coefficient of friction of between about 0.05 and about 0.4, or between about 0.1 and about 0.3, or about 0.2.

The PP comprising the cap 334 may have an elastic modulus of between about 500 MPa and about 1800 MPA, or between about 800 MPa and about 1500 Mpa, or about 1375 MPa. The PP may further have a tensile strength of between about 20 MPa and about 70 MPa, or between about 30 MPa and about 50 MPa, or about 35 MPa. The PP may further have a Poisson's ratio of between about 0.2 and about 0.6 or between about 0.3 and about 0.5, or about 0.42. The PP may further comprise a tangent modulus of between about 90 MPa and about 180 MPa, or between about 110 MPa and about 160 MPA, or about 140 MPa. The PP comprising the cap 334 may further comprise a coefficient of friction of between about 0.05 and about 0.4, or between about 0.1 and about 0.3, or about 0.2.

Figure 10:
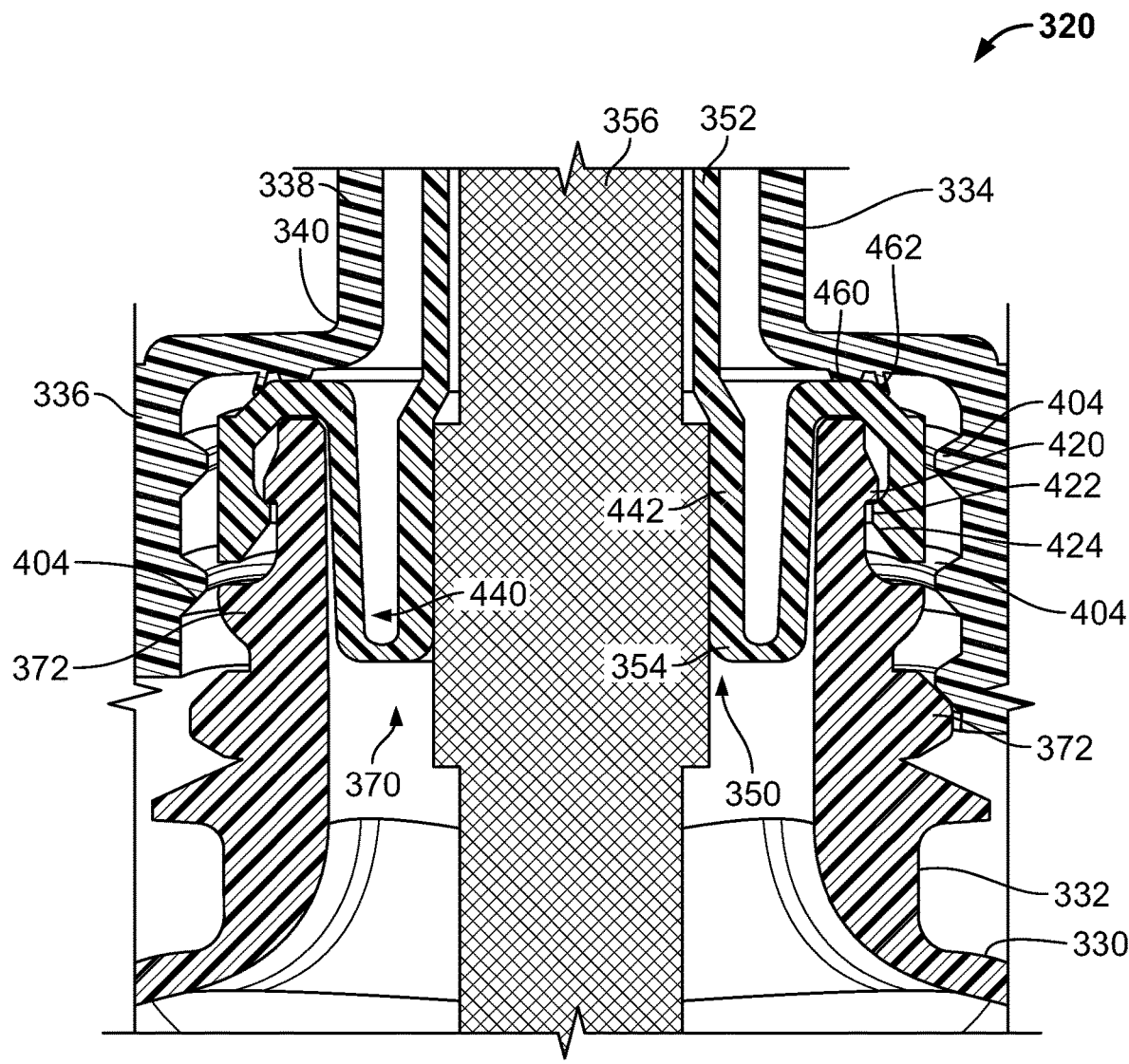
FIG. 10 is a cross-sectional view taken generally along the lines 10-10 of FIG. 9.

Referring to FIG. 10, a front cross sectional view of the refill 320 is shown. As illustrated therein, the refill 320 further includes a plug assembly 350 that is disposed within and is coupled to the neck 332 of the refill 320. The plug assembly 350 generally includes a sheath 352 and a base 354. The plug assembly 350 retains a wick 356 centrally within the bottle 330 and prevents leakage of volatile material out of the bottle 330. The wick 356 may have a similar configuration as the wick 56 of the refill 20 described above. The sheath 352 of the plug assembly 350 extends upwardly from a mouth 370 of the bottle 330 and surrounds a portion of the wick 356. The wick 356 may be any type of transportation mechanism such as, for example, typical wicks (of porous material), dip tubes, hollow tubes, and gravity fed surfaces or components, or any other suitable transportation mechanism. The plug assembly 350 may be comprised of polypropylene with similar characteristics as noted above.

Figure 11:
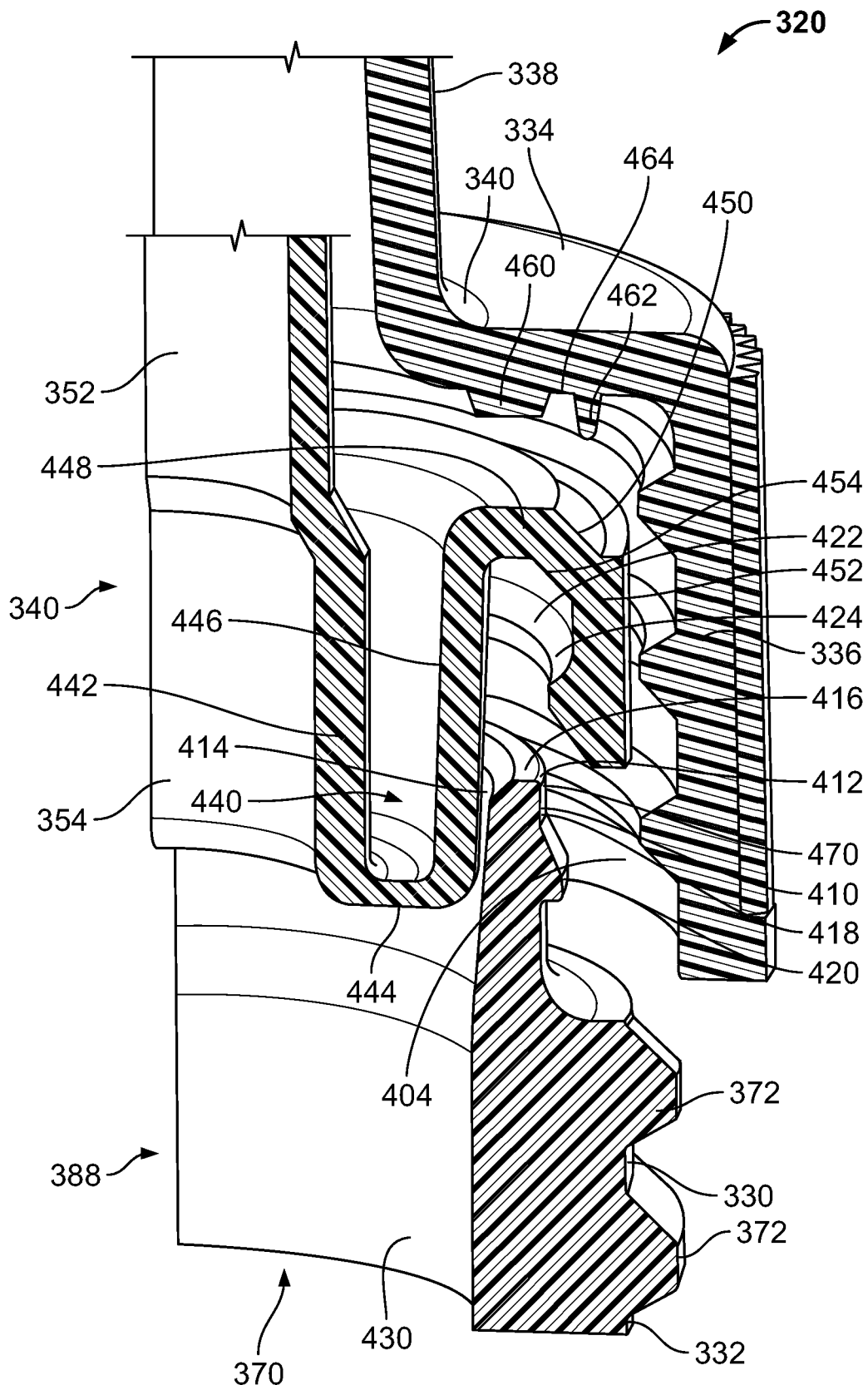
FIG. 11 is a partial cross-sectional view of the refill of FIG. 10, without a wick, and in an exploded or disassembled configuration.
Figure 12:
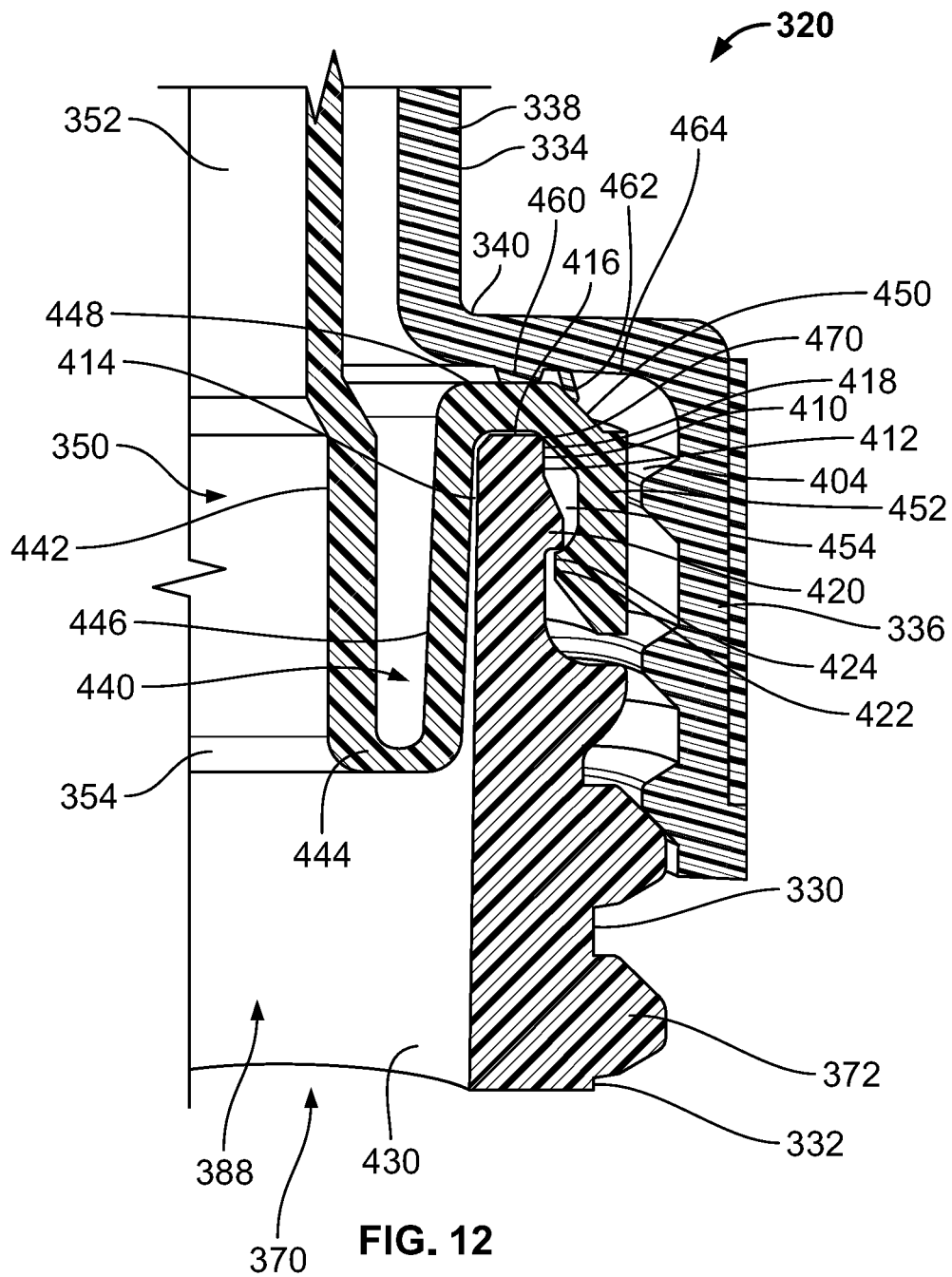
FIG. 12 is another partial cross-sectional view of the refill of FIG. 10, without a wick, and in an assembled configuration.
Figure 13:
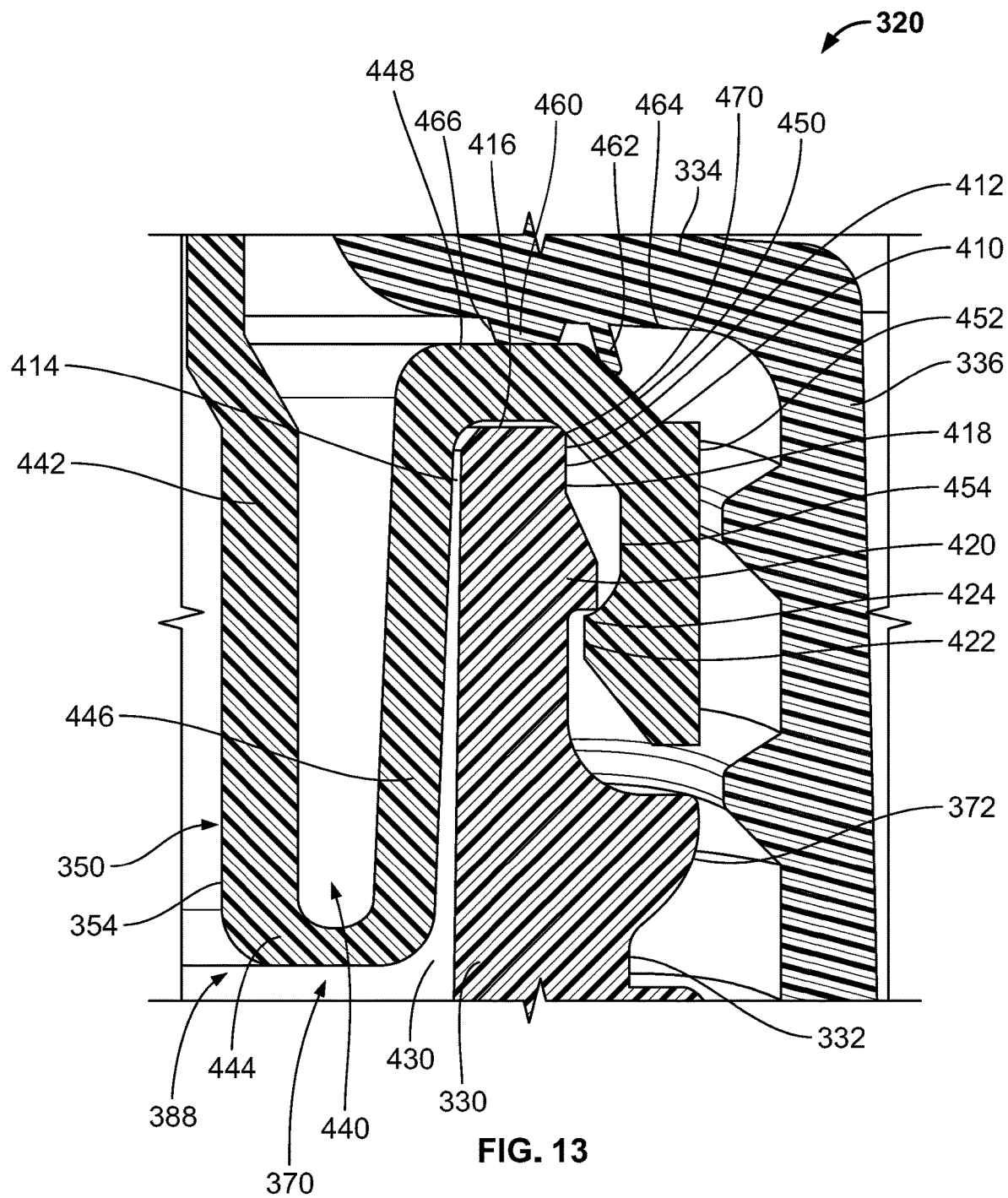
FIG. 13 is a detail, partial cross-sectional view of the refill of FIG. 10.

Referring now to FIGS. 11-13, a first thread 372 is disposed on the neck 332 of the bottle 330 to aid in retaining the cap 334 thereon and/or to aid in retaining the refill 320 within the dispenser. The cap 334 includes a second thread 404 along an inner surface thereof that corresponds to, and is operable to receive the first thread 372. The first thread 372 and the second thread 404 comprise a securement mechanism that may retain the cap 334 on the bottle 330. In other embodiments, other securement mechanisms may be utilized to retain the cap 334 on the bottle 330. The first and/or second threads 372, 404 may include a single start thread, a double start thread, or some other type of multi-start thread. The first and/or second threads 372, 404 may alternatively be discontinuous.

In embodiments where the bottle 330 includes a single start thread, a single "ridge" or thread wraps around the neck 332. Each full rotation of the cap 334 about the neck 332 causes the cap 334 to axially advance by the width of one ridge or thread. If the first and/or second threads 372,404 comprise a single start thread, each of the first thread 372 and the second thread 404 typically comprise a single spiraled helix. In these embodiments, the threading along one side of the neck 332 is necessarily vertically disposed below the threading along the other side of the neck 332 by ½ of the pitch of the threading, i.e., the distance from one crest of a thread to another thread above or below. This difference in the height of the threading can cause a tilt of the cap 334 when twisted on to a neck, as discussed in greater detail hereinafter below.

Referring to FIGS. 11 and 12, which illustrate the refill 320 in a partially exploded or disassembled configuration and an assembled configuration, respectively, an annular rim 410 is disposed at an upper end 412 of the neck 332, above the first thread 372. The rim 410 is defined by an interior surface 414, a top surface 416, and an outer surface 418, which will be discussed in greater detail hereinafter below. A first annular protrusion 420 extends outwardly from the neck 332 between the outer surface 418 of the rim 410 and the first thread 372.

In some embodiments, the first annular protrusion 420 is included to retain the plug assembly 350, which may include a locking feature 422, as shown in FIGS. 11-13. The locking feature 422 may include a second annular protrusion 424 that snaps over the first annular protrusion 420. The neck 332 of the bottle 330 also includes an inner surface 430 that forms a channel 388. While the first and second annular protrusions 420, 424 are described as being annular, the first and second annular protrusions 420, 424 may alternatively be discrete, discontinuous protrusions, similar to the above-described alternative configurations of the first and second annular protrusions 120, 124.

Still referring to FIGS. 11 and 12, the base 354 of the plug assembly 350 is shown in greater detail. The base 354 includes a well 440, similar to the well 140 described above, which is defined by a first or inner wall 442, a second or lower wall 444, and a third or intermediate wall 446. The inner wall 442 and the intermediate wall 446 are substantially parallel. The lower wall 444 joins the inner wall 442 with the intermediate wall 446 and is further substantially perpendicular to each of the inner wall 442 and the intermediate wall 446. A fourth or upper wall 448 is joined with, and extends outwardly from the intermediate wall 446. The upper wall 448 is coupled with a fifth or angled wall 450, which extends downward and outward, away from the upper wall 448. The angled wall 450 is joined with a sixth or outer wall 452, which is substantially perpendicular to the upper wall 448, and is substantially parallel with the inner wall 442 and the intermediate wall 446. The angled wall 450 may extend at an angle of between about 20 degrees and about 70 degrees, or between about 30 degrees and about 60 degrees, or about 45 degrees offset from a plane defined by the upper wall 448.

Continuing to refer to FIGS. 11 and 12, the second annular protrusion 424 is disposed along an inner surface 454 of the outer wall 452. In some embodiments, the inner wall 442, the intermediate wall 446, and the outer wall 452 are substantially parallel with respect to one another. Any wall or portion defined herein that is referred to as being substantially parallel with respect to another wall or portion may be up to 10 degrees offset from an axis defined by the first wall or portion.

Still referring to FIGS. 11 and 12, a stop or annular bead 460 and a wiper or annular flange 462 are included along an underside 464 of the cap 334. The annular flange 462 can be deflected (or fluted) to generate a compressive seal between the cap 334 and the plug assembly 350. As shown in FIG. 11, where the plug assembly 350 is illustrated being separated from the bottle 330, the annular flange 462 is disposed in a generally straight or vertical position, while in FIG. 12, which illustrates the plug assembly 350 assembled to the bottle 330, the annular flange 462 is shown in a deflected or angled configuration. Necessarily, during assembly of the refill assembly 320, when the plug assembly 350 is assembled to the bottle 330, the annular flange 462 is deflected outward, thereby acting, in part, as a spring, by applying an inward and/or downward force along the angled wall 450. The stop 460 may be included along the underside 464 of the cap 334 to prevent over-extension of the annular flange 462 when the cap 334 is coupled to the bottle 330.

The resultant potential energy of the flexed flange 462 as well as the orientation of the annular flange 462 in relation to the plug assembly 350, has been found to substantially reduce tensile stress along portions of the plug assembly 350. Specifically, inclusion of the annular flange 462 along an underside 464 of the cap 334 was found to reduce tensile stress along the outer wall 452 of the plug assembly 350 and reduce compressive stress along the upper end 412 of the neck 332 of the bottle 330. The inclusion of the annular flange 462 circumferentially about the underside 464 of the cap 334 and abutting the chamfered wall 450 allows for maintaining a viable 360 degree compressive seal between the cap 334 and the plug assembly 350. This may be particularly advantageous when the cap 334 utilizes a single start threading, which may result in the cap 334 not being completely parallel with respect to a plane defined through the top surface 416 of the rim 410 when the cap 334 is fully coupled with the bottle 330.

Effectively, the use of a single start threading may cause the cap to tilt or be offset with respect to an axis defined through the wick 356. As a result of the partial tilt of the cap 334 due to the threading, the inclusion of the annular flange 462 and the chamfered wall 450 has been found to allow for a wider range of threading that can be used, since the interface of the annular flange 462 and the chamfered wall 450 may vary circumferentially about the cap 334.

Referring now specifically to FIG. 12, where the plug assembly 350 is illustrated in an assembled configuration, the plug assembly 350 forms a compressive seal with the neck 332 of the bottle 330 by utilizing a snap over design that provides for a secure attachment to the bottle 330 by mechanical snap interference. The snap interference generates a fluid seal with a reduced tensile hoop stress in the neck 332 of the bottle 330 that would otherwise be generated during the sheath to bottle assembly in the absence of the plug assembly 350. Because of the inclusion of the angled wall 450, the second annular protrusion 424 can more easily snap over the first annular protrusion 420 to generate a desired compressive load and/or seal onto an outer shoulder 470 of the neck 332 of the bottle 330. This results in a desired compressive seal between the plug assembly 350 and the bottle 330 without imparting significant tensile stress to the neck 332.

Still referring to FIG. 12, the stop 460 is shown abutting the upper wall 448 of the plug assembly 350, and the flange 462 is shown in a deflected state and abutting the angled wall 450 of the plug assembly 350. The stop 460 acts to prevent overextension of the cap 334, as discussed above, and may also create a fluid tight seal, while the flange 462 operates to induce a compressive stress upon the plug assembly 350, and thus, the neck 332 of the bottle 330, which reduces stress cracking within the neck 332 of the bottle 330. In some embodiments, the stop 460 is provided directly above the rim 410. In some embodiments, the flange 462 is provided farther away from the wick than the stop 460. In some embodiments, an additional feature, such as a flange or a stop, is provided adjacent the stop 460 and/or the flange 462, such that the additional feature may be closer to the wick than the stop 460, may be disposed between the stop 460 and the flange 462, or may be farther from the wick than the flange 462. The stop 460 further defines an innermost stop surface 466, which is a surface of the stop that is closest to the wick 356.

As shown in FIG. 13, the plug assembly 350 is secured to the bottle 330, and the cap 334 is secured to the plug assembly 350. A first seal is formed between the stop 460 and the plug assembly 350 and/or the flange 462 and the plug assembly 350, which is referred to as the "sheath-to-cap" seal. A second seal is formed between the outer shoulder 470 of the neck 332 and the angled wall 450 (see FIG. 13), and/or between the top wall 448 and the top surface 416 of the rim 410, and/or between the intermediate wall 446 and the inner wall 430 of the neck 332, any of which are referred to as the "sheath-to-neck" seal. The sheath-to-cap seal and the sheath-to-neck seal prevent volatile material from escaping from the refill 320 when the cap 334 is secured to the bottle 330, and when the plug assembly 350 is secured to the bottle, respectively. As such, each of the sheath-to-cap seal and the sheath-to-neck seal may be an air tight seal.

Any of the embodiments described herein may be modified to include any of the structures or methodologies disclosed in connection with different embodiments. Further, the present disclosure is not limited to substrate and/or support component shapes/sizes of the type specifically shown. Still further, the support components of any of the embodiments disclosed herein may be modified to work with various types of substrates consistent with the disclosure herein.

INDUSTRIAL APPLICABILITY

Numerous modifications to the present disclosure will be apparent to those skilled in the art in view of the foregoing description. Accordingly, this description is to be construed as illustrative only and is presented for the purpose of enabling those skilled in the art to make and use the device disclosed herein and to teach the best mode of carrying out same. The exclusive rights to all modifications which come within the scope of the appended claims are reserved.

We claim:

1. A refill for dispensing a volatile material, comprising:
a bottle comprising polyethylene terephthalate (PET) and having:
a body defined by at least one sidewall; and
a neck extending from the body, the neck comprising a rim at an upper end thereof, wherein the rim is defined by at least an inner surface, a top surface, and an outer surface,
a wick having a first end positioned within the bottle and a second end extending out of the bottle;
a plug assembly comprising a first wall and a second wall, the second wall being angled with respect to the first wall, the plug assembly being secured to the neck of the bottle and retaining the wick within the bottle; and
a cap coupled with the neck of the bottle, an underside of the cap comprising a stop and a flange that form a seal with the plug assembly when the refill is in an assembled configuration, wherein the stop defines an innermost stop surface,
wherein the stop forms a seal with the first wall and the flange forms a seal with the second wall,
wherein the stop is disposed between the flange and the wick, and is provided directly above the rim when the refill is in the assembled configuration, and
wherein the inner surface of the rim is located radially closer to the wick than the innermost stop surface of the stop.

2. The refill of claim 1, wherein the plug assembly comprises an inner wall and an intermediate wall.

3. The refill of claim 2, wherein the inner wall is connected to the intermediate wall via a lower wall, and the first wall extends outward from the intermediate wall to join the second wall.

4. The refill of claim 3, wherein the flange of the cap is in contact with the second wall when the cap is coupled with the neck of the bottle.

5. The refill of claim 3, wherein the second wall is joined with an outer wall, the outer wall, the intermediate wall, and the inner wall of the plug assembly being substantially parallel with respect to one another.

6. The refill of claim 3, wherein the second wall is angled about 45 degrees offset from a plane defined by the first wall.

7. The refill of claim 1, wherein the cap is threadably coupled with the neck of the bottle.

8. The refill of claim 1, wherein the stop defines a lower surface that is planar.

9. The refill of claim 1, wherein a volatile material including at least one fragrance oil is disposed within the body of the bottle.

10. The refill of claim 1, wherein a first annular protrusion is disposed along the outer surface of the rim between threading along the neck and the top surface of the rim, the first annular protrusion configured to interact with a second annular protrusion on the plug assembly to secure the plug assembly on the neck of the refill.

11. A refill for dispensing a volatile material, comprising:
a bottle comprising polyethylene terephthalate (PET) and having:
a body defined by at least one sidewall; and
a neck extending from the at least one sidewall, the neck comprising:
threading circumscribing at least a portion of the neck; and
a rim at an upper end of the neck, the rim defined by at least an inner surface, an outer surface, and a top surface extending between the inner and outer surfaces;
a channel formed by the neck, a longitudinal axis being defined by the channel;
a wick having a first end positioned within the bottle and a second end extending out of the bottle, the wick being positioned within the channel;
a plug assembly coupled to the neck of the bottle, the plug assembly retaining the wick within the bottle; and
a cap attached to the bottle, the cap comprising a stop and a flange that depend from an underside of the cap, wherein the stop defines an innermost stop surface,
wherein the stop applies a force against a first wall of the plug assembly when the cap is attached to the bottle,
wherein the flange applies a force against a second wall that extends from the first wall,
wherein the first wall is angled with respect to the second wall,
wherein the stop is disposed between the flange and the wick, and is provided directly above the rim when the cap is attached to the bottle, and
wherein the inner surface of the rim is located radially closer to the wick than the innermost stop surface of the stop.

12. The refill of claim 11, wherein the plug assembly further comprises third and fourth walls that are spaced apart and positioned within the channel, a fifth wall connecting lower ends of the third and fourth spaced apart walls, the first wall connecting an upper end of the third wall with the second wall.

13. The refill of claim 12, wherein the second wall is angled between about 30 degrees and about 60 degrees from a plane defined by the first wall of the plug assembly.

14. The refill of claim 13, wherein a sixth wall extends from a lower end of the second wall, the sixth wall being parallel with respect to the third wall.

15. The refill of claim 11, wherein a first annular protrusion is disposed along the outer surface of the rim between the threading and the top surface of the rim.

16. The refill of claim 15, wherein a second annular protrusion is disposed along the plug assembly, and
wherein the second annular protrusion snaps over the first annular protrusion to retain the plug assembly on the neck of the refill.

17. The refill of claim 11, wherein the inner surface of the rim is tapered at an angle of between 2 degrees and 8 degrees offset from the longitudinal axis.

18. The refill of claim 11, wherein the plug assembly comprises polypropylene (PP) and the cap comprises polypropylene (PP).

19. The refill of claim 11, wherein the second wall is angled at an angle of between about 30 degrees and about 60 degrees offset from the longitudinal axis.

20. The refill of claim 19, wherein the second wall is in direct contact with an outer shoulder of the rim to form a sheath-to-neck seal.

* * * * *